United States Patent
Yoshida

(10) Patent No.: US 8,289,502 B2
(45) Date of Patent: Oct. 16, 2012

(54) MEASUREMENT APPARATUS AND MEASUREMENT METHOD

(75) Inventor: Hirofumi Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 443 days.

(21) Appl. No.: 12/558,773

(22) Filed: Sep. 14, 2009

(65) Prior Publication Data

US 2010/0073674 A1    Mar. 25, 2010

(30) Foreign Application Priority Data

Sep. 19, 2008    (JP) .................. 2008-241210

(51) Int. Cl.
*G01N 21/00*    (2006.01)

(52) U.S. Cl. ........................................... 356/73

(58) Field of Classification Search ............... 356/300, 356/72–73; 73/665; 702/56
See application file for complete search history.

(56) References Cited

U.S. PATENT DOCUMENTS

| | | | |
|---|---|---|---|
| 6,738,653 B1 | 5/2004 | Sfez et al. | 600/322 |
| 6,957,096 B2 | 10/2005 | Sfez et al. | 600/407 |
| 2009/0002685 A1* | 1/2009 | Fukutani et al. | 356/72 |
| 2009/0066949 A1 | 3/2009 | Masumura | |
| 2009/0069653 A1 | 3/2009 | Yoshida et al. | 600/323 |
| 2009/0069674 A1 | 3/2009 | Masumura et al. | 600/425 |
| 2009/0069685 A1 | 3/2009 | Nishihara et al. | 600/443 |

FOREIGN PATENT DOCUMENTS

| | | |
|---|---|---|
| JP | 2005-331292 | 12/2005 |
| JP | 2009-204430 | 8/2006 |
| JP | 2008-307372 | 12/2008 |
| JP | 2009-068962 A | 4/2009 |

* cited by examiner

*Primary Examiner* — Tarifur Chowdhury
*Assistant Examiner* — Abdullahi Nur
(74) *Attorney, Agent, or Firm* — Fitzpatrick, Cella, Harper & Scinto

(57) ABSTRACT

A measurement apparatus includes a DOT measurement unit, an AOT measurement unit, and a controller configured to calculate at least one of an absorption characteristic and a scattering characteristic of a test region set in an test object by utilizing one of the DOT measurement unit and the AOT measurement unit, whichever one has the smaller measurement size.

12 Claims, 9 Drawing Sheets

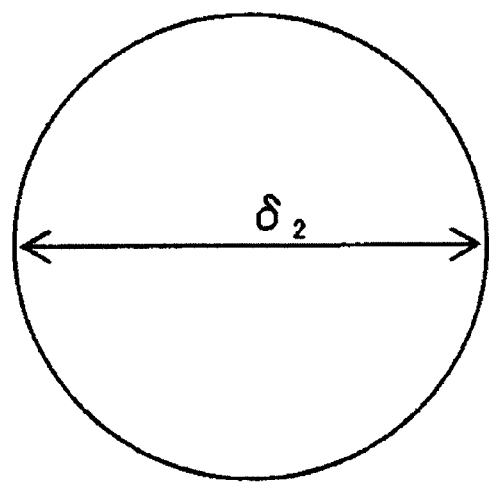
FIG. 6
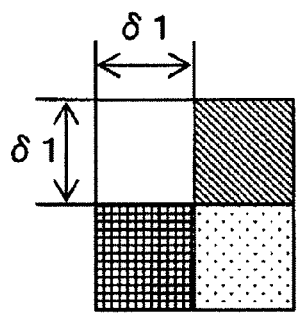 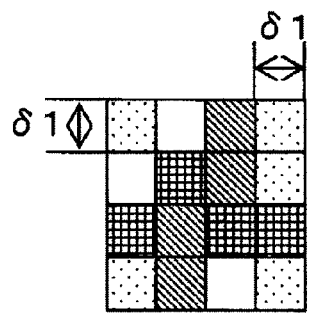 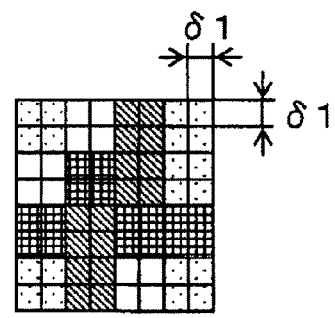
FIG. 7A    FIG. 7B    FIG. 7C

MEASUREMENT APPARATUS AND MEASUREMENT METHOD

BACKGROUND OF THE INVENTION

1. Field of the Invention

The present invention relates to a measurement apparatus and a measurement method.

2. Description of the Related Art

Diffused optical tomography ("DOT") and acousto-optical tomography ("AOT") are known techniques for measuring a spectroscopic characteristic of a biological tissue. The spectroscopic (or attenuation) characteristic contains an absorption (spectroscopic) characteristic and a scattering (spectroscopic) characteristic, and at least one of the absorption characteristic and the scattering characteristic (which will be also referred to as an "absorption-scattering characteristic" hereinafter) is necessary to measure the biological tissue with a high resolution.

DOT introduces near-infrared light to a test object and detects diffused light, as described in Japanese Patent Laid-Open No. ("JP")2005-331292. AOT irradiates coherent light and focused ultrasonic waves into the test object, and utilizes an effect of light modulation (acousto-optical effect) due to the interaction between the light and the ultrasonic wave in an ultrasonic focus region (test region), as disclosed in U.S. Pat. No. 6,738,653. JP 2005-331292 assumes the internal distribution of the spectroscopic characteristic and employs an algorithm that is used to modify or reconstruct the assumption in accordance with the measurement result, but the calculation of the internal distribution is complex, an enormous and time-consuming process, and unlikely to converge quickly to the optimal solution. Therefore, U.S. Pat. No. 6,957,096 proposes to partially obtain the spectroscopic characteristic utilizing AOT and to utilize it for the solution.

Since AOT focuses ultrasonic waves in the test region in the test object, the resolution of the test region of AOT is superior to that of DOT because the measurement size of AOT is smaller. However, the light intensity detected by the photodetector in AOT is lower than that in DOT due to focusing. Since the photodetector cannot detect the light unless the light intensity is higher than a threshold, the light intensity becomes too small for AOT measurement as a distance of the test region from the surface of the test object increases. The increased surface area of the focused ultrasonic waves in AOT can overcome the light intensity deficiency, but will result in a deterioration of the resolution. Conventionally, a solution for this problem is not proposed.

SUMMARY OF THE INVENTION

The present invention provides a measurement apparatus and a measurement method which can more precisely measure a spectroscopic characteristic of a test object by utilizing AOT and DOT than a single use of AOT.

A measurement apparatus according to one aspect of the present invention includes a first measurement unit configured to measure a spectroscopic characteristic inside of an object that is an absorption-scattering medium, by applying diffused light tomography, a second measurement unit configured to measure the spectroscopic characteristic inside of the object by applying acousto-optical tomography, and a controller configured to calculate at least one of an absorption characteristic and a scattering characteristic of a test region that is set in the object by utilizing one of the first measurement unit and the second measurement unit, whichever one has the smaller measurement size.

A measurement method according to another aspect of the present invention includes calculating at least one of an absorption characteristic and a scattering characteristic of a test region that is set in a object that is an absorption-scattering medium, using a first measurement unit that is configured to measure a spectroscopic characteristic in the test object utilizing diffused light tomography and that includes a photodetector configured to detect light that has passed inside the object and is emitted from the object, calculating at least one of the absorption characteristic and the scattering characteristic of the test region in the object using a second measurement unit that is configured to measure the spectroscopic characteristic in the object utilizing acousto-optical tomography, and that includes an ultrasonic transducer configured to focus and irradiate ultrasonic waves upon the test region in the object, obtaining a size of a mesh that is a division unit of the test region, obtaining a focus diameter of an ultrasonic focus region from the ultrasonic transducer, and selecting one of the first measurement unit and the second measurement unit, whichever one has the smaller measurement size from the size of the mesh and the focus diameter.

Further features of the present invention will become apparent from the following description of exemplary embodiments with reference to the attached drawings.

BRIEF DESCRIPTION OF THE DRAWINGS

FIG. 6 is a schematic plane view showing a focus diameter as a diameter of an ultrasonic focus region shown by FIG. 1B.

FIGS. 7A-7C are plane views for explaining a mesh size determined by S9-S16 in FIG. 5.

DESCRIPTION OF THE EMBODIMENTS

A description will be given of embodiments of the present invention.

First Embodiment

Figure 1A:
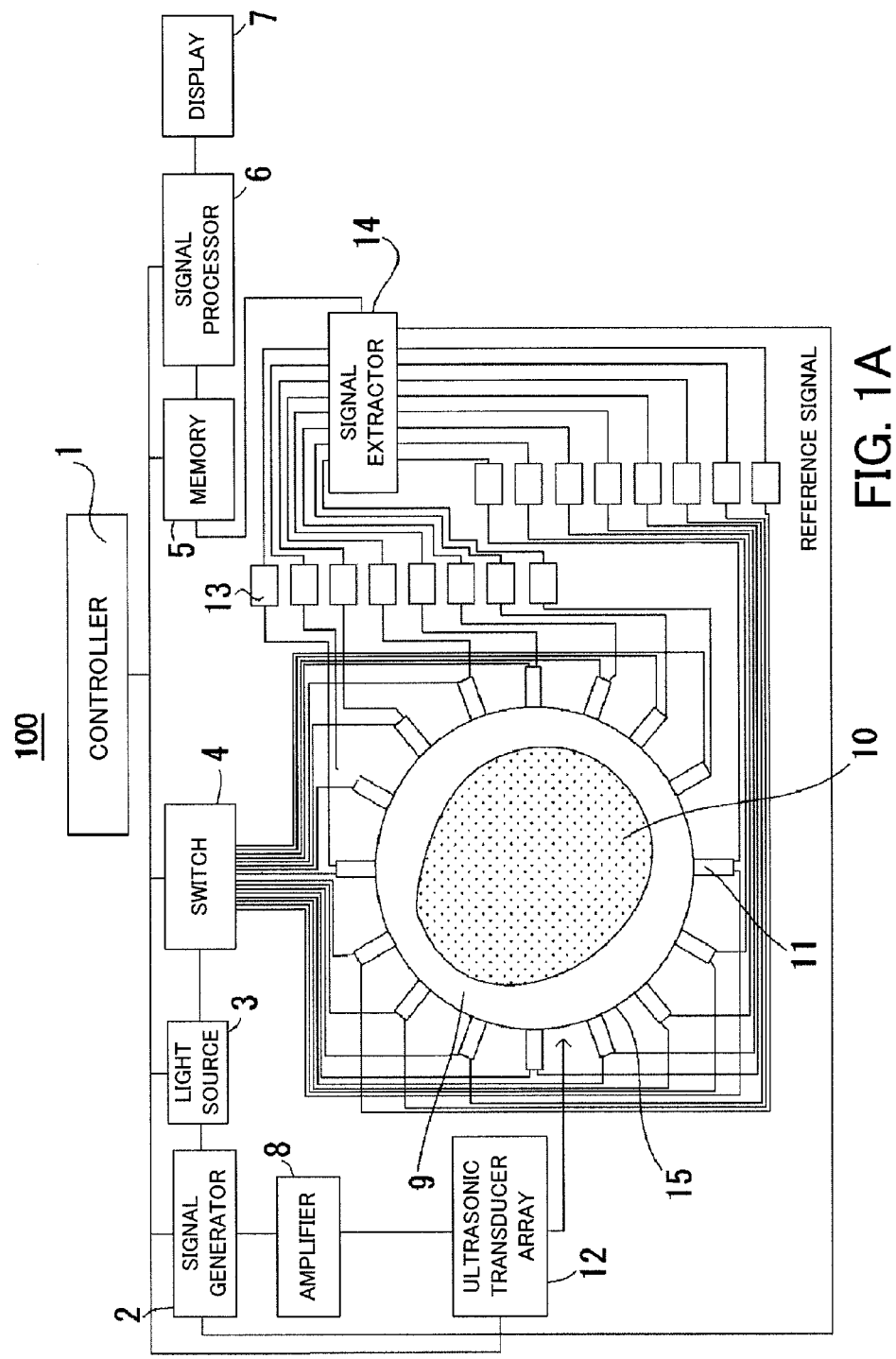
FIGS. 1A-1C are block diagrams of a measurement apparatus according to a first embodiment.
Figure 1B:
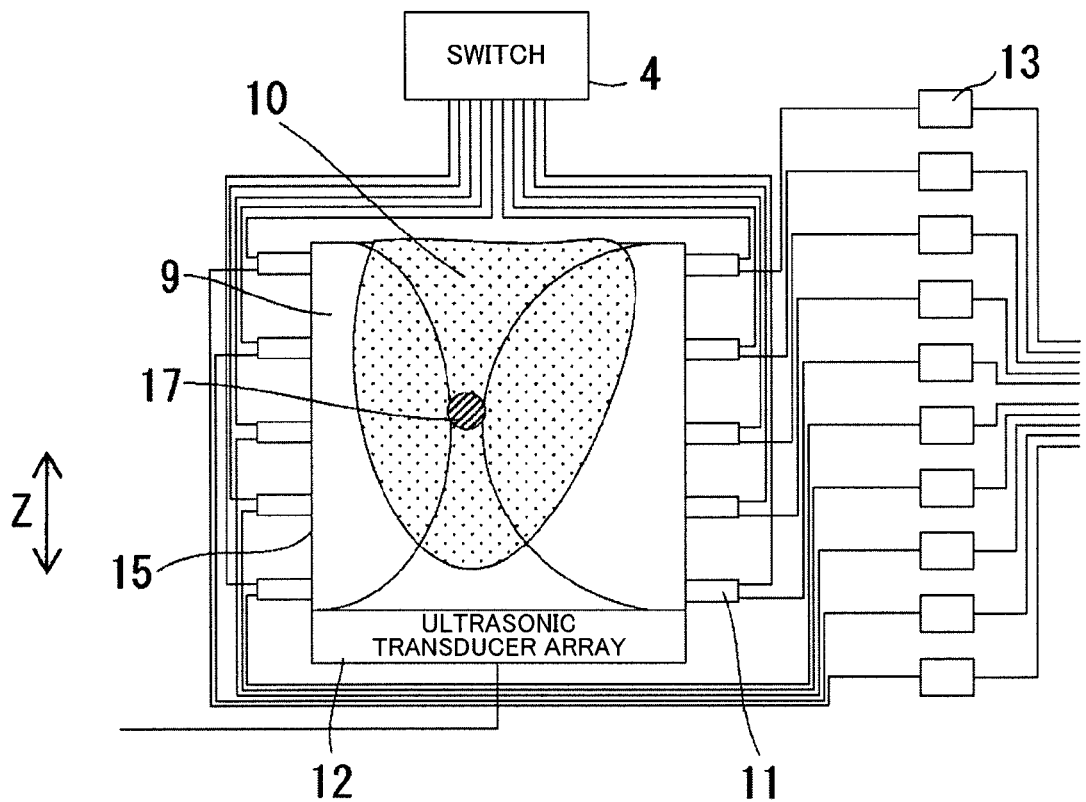
Figure 1C:
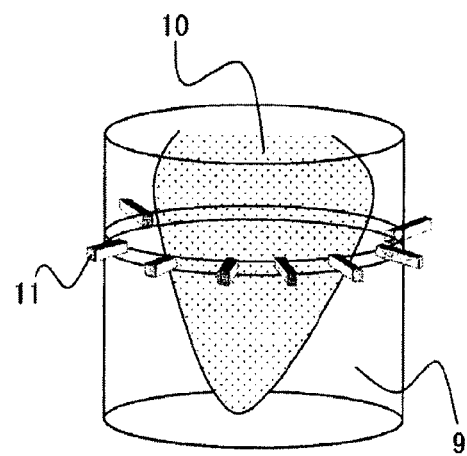

FIGS. 1A-1C are block diagrams of a measurement apparatus 100 according to a first embodiment. The measurement apparatus 100 measures a spectroscopic characteristic in a tissue of a test object 10, such as a breast, by utilizing both AOT and DOT. The measurement apparatus 100 includes a controller 1, a signal generator 2, a light source 3, a switch 4, a memory 5, a signal processor 6, a display 7, an amplifier 8, a plurality of fibers 11, an ultrasonic transducer array 12, a plurality of photodetectors 13, a signal extractor 14, and a measurement container 15. FIG. 1A is a sectional view of the measurement container 15 that houses the test object 10, FIG. 1B is its side view, and FIG. 1C is its perspective view.

The measurement apparatus 100 includes a first measurement unit and a second measurement unit. The controller 1 calculates at least one of a scattering characteristic and an absorption characteristic of the test region set in the test object 10 by utilizing one of the first measurement unit and the second measurement unit, which one has a higher resolution or a smaller measurement size of measuring the test region in the test object 10.

The first measurement unit is a DOT measurement unit configured to measure the spectroscopic characteristic in the test object 10 utilizing diffused optical tomography. The first measurement unit includes the signal generator 2, the light source 3, the switch 4, the fibers 11, and the photodetectors 13 in addition to the control system and the signal processing system.

The second measurement unit is an AOT measurement unit configured to measure the spectroscopic characteristic in the test object 10 by utilizing acousto-optical tomography. The second measurement unit includes the signal generator 2, the light source 3, the switch 4, the amplifier 8, the fibers 11, the ultrasonic transducer array 12, the photodetectors 13 in addition to the control system and the signal processing system.

Thus, the first measurement unit and the second measurement unit are incorporated into one measurement apparatus, but they may share some components or may be two completely separate units.

The test object 10 of this embodiment is an absorption-scattering medium to be housed in the cylindrical measurement container 15. The Z-direction shown in FIG. 1B is a height direction in which the test object 10 extends and, for example, is perpendicular to a surface of the bed (not shown) on which a woman lies face down. A homogeneous medium (matching material) 9 having a known characteristic is used to fill in the space between the test object 10 and the measurement container 15, and has a refractive index defining its response to the light used and an acoustic characteristic defining its response to ultrasonic waves equivalent to the test object 10. However, the matching material 9 may be omitted from the space between the test object 10 and the measurement container 15 on a section in which the test object 10 contacts the internal surface of the measurement container 15.

In the first or DOT measurement unit, the signal generator 2 generates a sine signal having a frequency f1. The sine signal generated by the signal generator 2 is used to drive the light source 3. In general, in a biological measurement, a sine signal is modulated in intensity with a sine wave of dozens to hundreds of MHz. The light source 3 may utilize one that can supply coherent light, such as a laser, and may employ a light source configured to generate light beams of a plurality of wavelengths or may switch a plurality of light sources for each wavelength. The wavelength in the light source is selected among wavelengths in accordance with absorption spectra such as water, lipid, protein, oxygenated hemoglobin, and reduced hemoglobin. In an example, an appropriate wavelength falls upon a range between 600 and 1,500 nm, because light in that range is transmitted at a high rate due to its small absorption by water, which is a main ingredient of the internal biological tissue, and the spectra of the lipid, the oxygenated hemoglobin, and the deoxygenated hemoglobin are characteristic. The signal from the signal generator 2 modulates the light from the light source 3, and generates intensity-modulated light. The intensity-modulated light is introduced to a plurality of fibers 11. Each fiber 11 is connected to the side surface of the measurement container 15, and the switch 4 is provided between the measurement container 15 and the light source 3.

The switch 4 has an opening and closing function, such as a shutter, and is operated so that the light from the light source 3 enters one fiber 11 designated by the controller 1 among the n fibers 11. The light from the light source 3 is shielded by the shutter from the other (n−1) fibers 11. The (n−1) fibers 11 introduce to the photodetectors 13 the diffused light that has been radiated from the side surface of the measurement container 15, and passed the test object 10 and the matching material 9. The fiber 11 configured to introduce the light from the light source 3 to the measurement container 15 is closed by the shutter so as not to introduce the diffused light to the photodetectors 13. One fiber that introduces the light from the light source 3 to the measurement container 15 is exclusive to the (n−1) fibers 11 configured to introduce the diffused light from the measurement container 15 to the photodetectors 13. The light incident upon the inside of the measurement container 15 from the fiber 11 propagates as diffused light in a variety of directions after the light repeats the absorptions and scatters in the matching member 9 and the test object 10.

The light propagation in the absorption-scattering medium, such as the test object 10 and the matching member 9, can be described by the light diffusion equation. A fluence rate of photons at a position "r" at time "t" in the absorption-scattering medium can be expressed as follows:

$$\frac{\partial \Phi(r, t)}{\partial t} = D' \nabla^2 \Phi(r, t) - v\mu_a \Phi(r, t) + vS(r, t) \qquad \text{Equation 1}$$

$\Phi(r, t)$ is the fluence rate of photons [the number of photons/(mm$^2$/sec)]. $D'$ ($=v/3\mu_s'$) is an equivalent diffusion coefficient [mm$^2$/sec]. $\mu_s'$ is an equivalent scattering coefficient [1/mm]. $v$ is the light speed in the test object [mm/sec]. $\mu_a$ is an absorption coefficient [1/mm] $S(r, t)$ is a radiation photon flux density of the light source [the number of photons/(mm$^2$·sec)].

The intensity-modulated light incident upon the measurement container 15 from the fiber 11 propagates as the energy density wave of a frequency f1 in the absorption-scattering medium, which is referred to as the diffused photon density wave, as derived from the Equation 1. A light intensity $I_{AC}(r, \omega)$ and phase $\Theta(r, \omega)$ of this diffusion photon density wave is expressed as follows:

$$I_{AC}(r, \omega) = \frac{vS_0}{4\pi Dr} \exp\left[-r\left(\frac{v\mu_a}{2D}\right)^{1/2}\left\{\left(1 + \frac{\omega^2}{v^2\mu_a^2}\right)^{1/2} + 1\right\}^{1/2}\right] \qquad \text{Equation 2}$$

$$\Theta(r, \omega) = r\left(\frac{v\mu_a}{2D}\right)^{1/2}\left\{\left(1 + \frac{\omega^2}{v^2\mu_a^2}\right)^{1/2} - 1\right\}^{1/2} + \phi_0 \qquad \text{Equation 3}$$

Here, $\omega$ ($=2\pi f1$) is the angular frequency [rad/sec] of the intensity-modulated wave, $S_0$ is the number of incident photons per unit time [the number of photons/sec], and $\Phi_0$ is the phase [rad] of the light source.

The light intensity of this diffused photon density wave is detected by the photodetectors 13 through (n−1) fibers arranged around the side surface of the measurement container 15. Thus, the photodetector 13 detects the light that has passed through the inside of the test object 10 and exited to the outside, and the photodetector 13 converts the light into an electric signal. The signal converted by the photodetector 13 is transmitted to the signal extractor 14. The signal extractor 14 calculates the amplitude and phase of the diffusion photon density wave expressed by Equations 2 and 3 based on the signal sent as a reference signal from the signal generator 2. This is repeated for all (n−1) signals. As indicated by Equations 2 and 3, the amplitude and phase of the diffusion photon density wave depend upon the absorption coefficient and the scattering coefficient of the medium. In the first measurement unit, the test region is an area through which the diffused light passes in the test object 10.

The data concerning the amplitude and the phase calculated by the signal extractor 14 is sent to and stored in the memory 5. In addition to the measurement data, the measurement condition of the fiber 11 used as a light source is also stored in the memory 5. The measurement is repeated "n" times so that each of all "n" fibers can become a light source, and all measurement data is stored in the memory 5.

The fibers 11 may be arranged on the side surface of the measurement container 15 three-dimensionally. Alternatively, as shown in FIG. 1C, the three-dimensional data may be obtained by scanning a module arranged on a section in which a plurality of fibers 11 are two-dimensionally arranged, in a longitudinal direction of the side surface of the measurement container 15.

The above measurement will be referred to as a "first measurement," and the data obtained in the first measurement will be referred to as "first measurement data" hereinafter.

While the first measurement utilizes a measurement method that uses the intensity-modified light for the light source 3 and the diffusion photon density wave expressed by Equations 2 and 3 by solving the diffusion equation of Equation 1 for the frequency region, another measurement method may be utilized which uses pulsed light of picoseconds for the light source 3 for the time region of Equation 1.

After the first measurement ends, the signal processor 6 starts an image reconstruction by reading out the first measurement data from the memory 5. The signal processor 6 executes a process by sequentially reading out the data necessary for the image reconstruction from the memory 5. After the first measurement ends, the second measurement starts. The order in which these steps—the DOT measurement, the image reconstruction that determines the spectroscopic characteristic (i.e., the absorption characteristic and the scattering characteristic) and the measurement size in the DOT, and the AOT measurement—is not limited, and two of three, such as the image reconstruction and the second measurement, may be performed simultaneously.

In the second or AOT measurement unit, the controller 1 controls the signal generator 2 and emits continuous light from the light source 3. Similar to the above description, the modulated light is introduced to the fiber 11, and the controller 1 controls the switch 4 and selects one fiber 11 as the light source. The light from the light source 3 enters the side surface of the measurement container 15 through the selected fiber 11. The light incident upon the inside of the measurement container 15 propagates in the measurement container 15 and repeats the absorptions and scatters, similar to the above description.

At this time, the signal from the signal generator 2 is led through the controller 1 to the amplifier 8 and amplified there, so as to continuously drive the ultrasonic transducer array 12. The ultrasonic transducer array 12 operates individual ultrasonic transducers so that the ultrasonic wave can be focused upon the predetermined position (test region) in the measurement container 15 designated by the controller 1, and irradiates the focused ultrasonic wave having a frequency $\Omega$. In the ultrasonic focus region (test region) 17, the density of the medium changes, and the refractive index of the medium and the displacement of the scattering medium change in accordance with the frequency of the irradiated ultrasonic wave. After the light passes the ultrasonic focus region 17, the optical phase of the light changes due to the change of the refractive index and the displacement of the scattering medium. In the absorption-scattering medium, an intensity $\Psi(r_i)$ of the detected light that has passed the ultrasonic focus region at the position $r_i$ and received the ultrasonic modulating effect can be calculated from the following equation:

$$\Psi(r_i) = S_0 \Phi(r_s, r_i) m(\mu_a, \mu_s') A_m \Phi(r_i, r_d)$$ Equation 4

Here, $\Phi(r_s, r_i)$ is the fluence rate of photons from the position $r_s$ of the light source (light incident end) to the position $r_i$. $\Phi(r_i, r_d)$ is the fluence rate of photons from the position $r_i$ to the position $r_d$ of the detector. In addition, $m(\mu_a, \mu_s')$ is the ultrasonic modulation efficiency (interaction at the ultrasonic focus region 17). $A_m$ is the surface area of the ultrasonic focus area.

The light detected by the photodetector 13 includes the light that has passed through the ultrasonic focus region 17 and received the ultrasonic modulation, and the non-modulated light that is not subject to the ultrasonic modulation. The signal extractor 14 measures a modulated signal modulated by the ultrasonic frequency $\Omega$ expressed by Equation 4. The signal extractor 14 functions as a filter, and separates the modulated light and the non-modulated light from each other. In order to detect the signal efficiently, a band-pass filter configured to perform selective detection of a signal of a specific frequency, and a lock-in amplifier configured to amplify and detect the light of a specific frequency are applicable.

For example, when the photodetector 13 utilizes a photomultiplier tube ("PMT"), the signal extractor 14 measures the modulated light and the non-modulated light, and the signal processor 6 calculates the modulation depth M, which is an amplitude $I_1$ of the light intensity of the modulated light divided by the light intensity $I_1$ of the non-modulated light. Alternatively, when the photodetector 13 uses a CCD or a CMOS, the output signal is amplified and AD-converted, and the resultant data is delivered to the signal processor 6. The signal processor 6 calculates the modulation depth M from the speckle contrast when the ultrasonic wave irradiate and when the ultrasonic wave does not irradiate. The calculated modulation depth M is stored in the memory 5.

The signal processor 6 calculates a concentration and a component ratio of the gradients in the test object that contributes to the absorption of the spectroscopic characteristic. In addition, the signal processor 6 produces distribution data of the spectroscopic characteristic in the test object 10 by corresponding to the data relating the calculated spectroscopic characteristic to the coordinate data of the ultrasonic irradiation. The signal processor 6 also generates an image. The signal processor 6 generates a three-dimensional tomographic image of the test object 10 from the distribution data of the spectroscopic characteristic of the test object 10.

The memory 5 records data and an image of a spectroscopic characteristic generated by the signal processor 6. The memory 5 may use a data recording device such as an optical disc, a magnetic disc, a semiconductor memory, and a hard disk drive. The display 7 displays an image generated by the signal processor 6, and can use a display device such as a liquid crystal display, a CRT, and an organic EL.

An ultrasonic focus diameter $\delta_{v.s.}$ can be expressed by the following equation where $\Omega$ is the ultrasonic frequency, vs is the ultrasonic velocity of in the test object 10, B1 is a diameter of a driving area of the ultrasonic transducer array 12, and Z1 is a distance from the ultrasonic transducer array 12 to the ultrasonic focus position:

$$\delta_{V.S.} = 2.44 \cdot \frac{\Omega}{vs \cdot B1} \cdot z1 \qquad \text{Equation 5}$$

The ultrasonic focus position and focus diameter can be controlled by controlling a range of the thus driven ultrasonic transducer and a delay time given by a variable delay element. Electrically focusable search units include in addition to a two-dimensional array search unit, a linear array search unit having linearly arranged ultrasonic transducers, and an annular array search unit having concentrically arranged ring-shaped transducers. When a circular and concave ultrasonic transducer or an acoustic lens is used, the ultrasonic focus position can be controlled by changing positions of these members through mechanical driving.

The above measurement will be referred to as a "second measurement," and the modulated signal obtained in the second measurement will be referred to as "second measurement data." The second measurement data is stored in the memory 5 separate from the first measurement data. Similar to the first measurement, the memory 5 also stores parameters necessary for the subsequent image reconstruction, such as a fiber used as a light source, an ultrasonic focus position, and an ultrasonic intensity, for each second measurement data. The fiber 11 selected as a light source can be the fiber 11 close to the ultrasonic focus position so as to improve the intensity of the light modulated by the ultrasonic wave.

In order to improve the resolution, the ultrasonic transducer array 12 may be driven by a signal having a pulse width of a submicron second to several microseconds produced by the signal generator 2 rather than a continuous signal. After a plurality of ultrasonic focus positions are arbitrarily set in the measurement container 15, the second measurement is performed for each ultrasonic focus position and the obtained data is sent to the memory 5.

When the second measurement of the ultrasonic focus region 17 ends, the ultrasonic focus region is moved to an arbitrary different position and the second measurement is repeated. By repeating the second measurement sequentially, the absorption coefficient and the scattering coefficient of the entire test object 10 can be obtained.

Since the AOT focuses the ultrasonic wave upon the ultrasonic focus region 17 in the test object, the resolution of the AOT is superior to that of the DOT because the measurement size of the AOT is smaller. However, the light intensity of the AOT detected by the photodetector 13 is smaller than that of the DOT. Unless the light intensity is equal to or higher than a threshold, the photodetector cannot detect the light. It is understood from Equation 4 that as the distance from the surface of the test object 10 becomes longer, the light intensity $\Psi(r_i)$ can attenuate below the noise level of the photodetector 13. As a result, in such instance the photodetector 13 cannot measure the light. The light intensity $\Phi(r_i)$ increases as the surface area $A_m$ of the ultrasonic focus region 17 increases in the Equation 4. When it is assumed that Iw is a noise level of the photodetector 13, information on a deep part in the test object 10 can be extracted by calculating a minimum ultrasonic focus size that satisfies $\Phi(r_i)$>Iw from Equation 4, and by adjusting the surface area $A_m$ of the ultrasonic focus region 17 in accordance with the location.

On the other hand, in Equation 4, due to the modulation efficiency $m(\mu_a, \mu_s')$, the surface area $A_m$ of the ultrasonic focus region 17 of the AOT for a certain light intensity $\Phi(r_i)$ needs to be made larger than the surface area of the diffused light passage area of the DOT. Hence, depending upon the size, the absorption coefficient, and the scattering coefficient of the test object 10, the AOT is superior in resolution until the distance from the surface of the test object 10 becomes a predetermined threshold, and the DOT is superior in resolution when the distance becomes larger than the threshold. A detailed description will be given of the resolutions (measurement sizes) of the DOT and the AOT.

Figure 2:
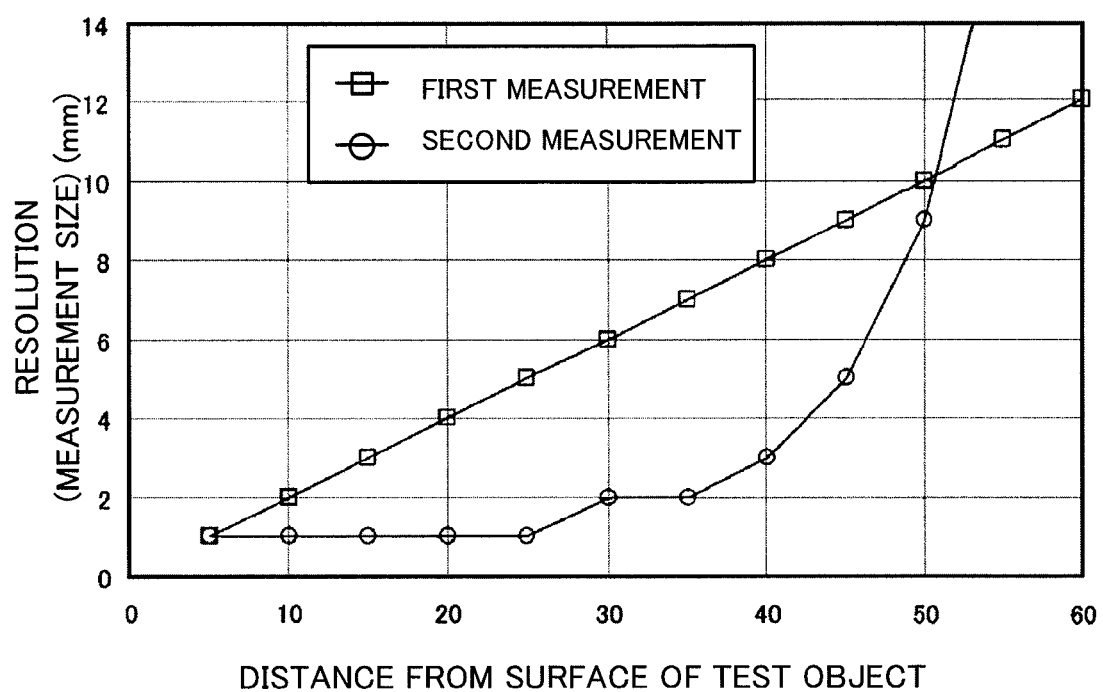
FIG. 2 is a graph showing a relationship between a distance of a test region from a surface of a test object and resolutions (measurement sizes) of a first measurement utilizing DOT and a second measurement utilizing AOT.

FIG. 2 is a graph having an ordinate axis of the resolution (measurement size) of each of the first measurement and the second measurement, and an abscissa axis of a distance of the test region from the surface of the test object 10. The measurement size of the first measurement linearly increases with the distance of the test region from the surface of the test object 10 since the measurement size is set to 10% of the optical path length from the general light source to the photodetector. On the other hand, the measurement size of the second measurement unit is determined by the obtainable light intensity, and adjusted by changing the ultrasonic focus diameter. Since the light attenuation increases as the optical path length increases, the ultrasonic focus diameter needs to be increased.

The light attenuation in the test object 10 is calculated by using Equation 4 and $\Phi(r_s, r_i)$ and $\Phi(r_i, r_d)$ with respect to a distance "d" from the surface of the test object 10. The absorption coefficient $\mu_a$ and the scattering coefficient $\mu_s'$ use biological mean values of 0.01 mm$^{-1}$ and 1 mm$^{-1}$. In addition, $m(\mu_a, \mu_s')$ becomes of the order of about $10^{-5}$. Under this condition, the light intensity that drops due to the light propagation when the distance of the test region from the surface of the test object 10 is increased is adjusted by increasing the surface area $A_m$ of the ultrasonic focus region 17.

Figure 3:
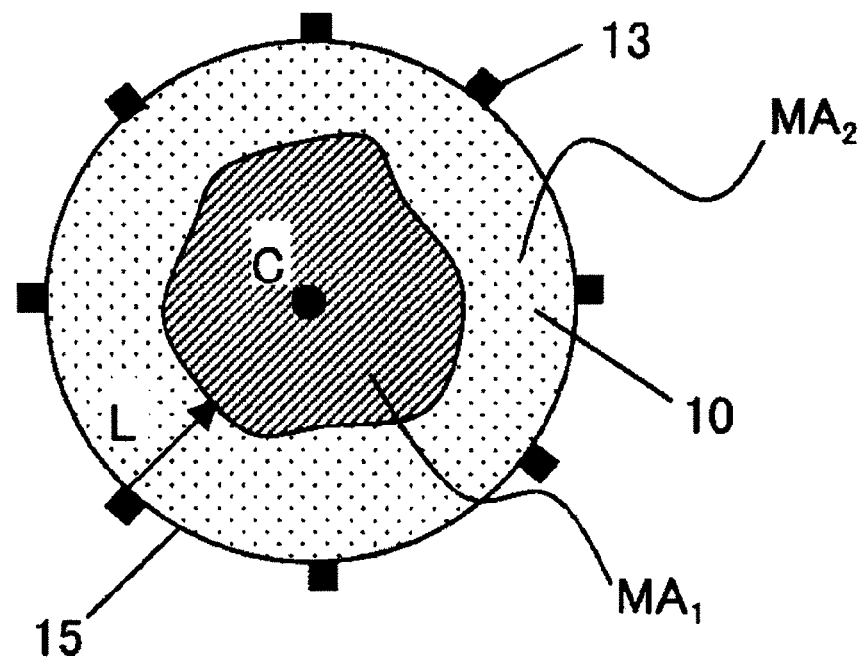
FIG. 3 is a sectional view of the test object showing a first measurement region and a second measurement region in the first embodiment.

FIG. 2 plots the size of the ultrasonic focus region 17 when the light intensity $\Psi(r_i)$ that is the detection limit of the photodetector 13 is set to 1 pW. While the light intensity of the detection limit of the photodetector 13 is set to 1 pW, a smaller measurement size can be obtained at the test region that is more distant from the surface of the test object 10 when the detection limit shifts from the relationship shown in FIG. 2 and becomes smaller depending upon the change of the measurement limit. In this case, the relationship does not become linear but increases like an exponential function as the optical path length increases. Therefore, the resolution of the second measurement is superior in the test region close to the surface of the test object 10, and the resolution of the first measurement unit comes to become superior in the test region as it becomes distant. Thus, a test region $MA_2$ closer to this intersection receives the second measurement, and a test region $MA_1$ distant from this intersection receives the first measurement. The region measured by the first measurement unit and the region measured by the second measurement unit in the test object 10 become as shown in FIG. 3, for example. For simplicity, FIG. 3 shows that the test object 10 spreads over the inside of the measurement container 15 with no matching member 9. "L" denotes the (shortest) distance of the test region from the surface of the test object 10 in a radial direction that connects the center C of the measurement container 15 or the test object 10 to the measurement container 15 on the section perpendicular to the height direction Z in which the test object 10 shown in FIG. 1B extends.

Figure 4:
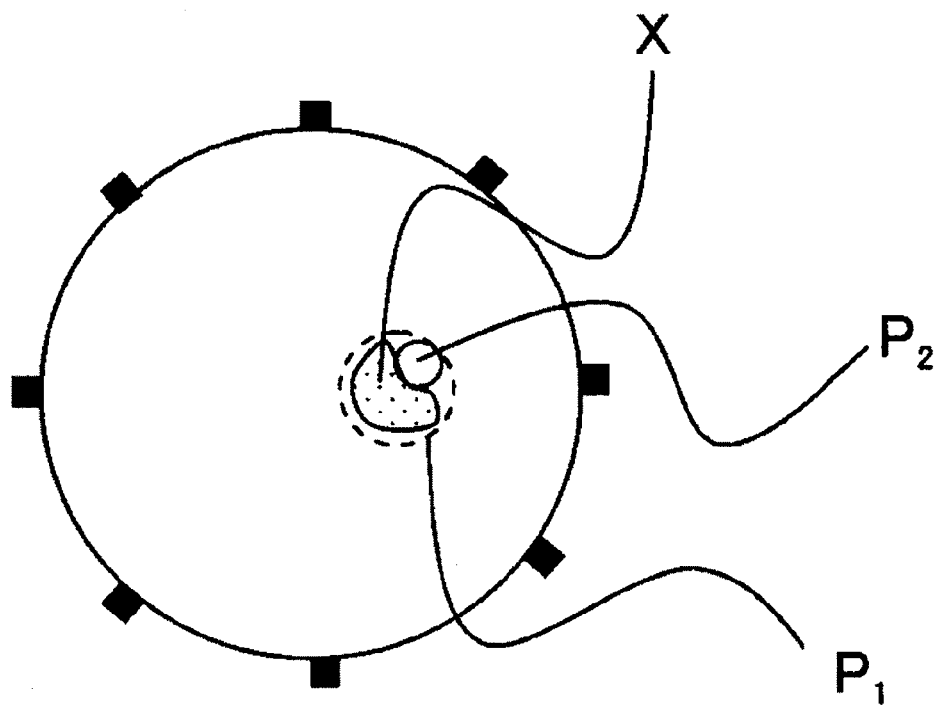
FIG. 4 is a sectional view of the test object showing that the first measurement region partially overlaps the second measurement region in the first embodiment.

An image conceivably falls in the test region that includes a border between the first measurement and the second measurement, and needs to be reconstructed with data having a larger measurement size. For example, assume an absorption object (test region) X such as a cancer in the test object 10, as shown in FIG. 4. A dotted-line circle indicates a region $P_1$ for the first measurement, and a solid-line circle indicates a region $P_2$ for the second measurement. The test region closer to the surface of the test object 10 receives the second measurement, and the measurement area more distant from the surface of the test object 10 than this region receives the first measurement. As shown in FIG. 4, when the first measurement region overlaps the second measurement region, the second measurement is performed and an image outside of the region $P_2$ in the region $P_1$ breaks. Therefore, it is necessary to reconstruct or supplement the region other than the overlap portion of the circle by using the measurement result of the first measurement unit.

As described above, the AOT is superior in resolution when the distance of the test region from the surface of the test object 10 is from zero to the predetermined threshold and the DOT is superior in resolution when the distance of the test region is larger than the threshold. This embodiment switches a measurement technique that is superior in resolution according to the distance from the surface of the test object.

Figure 5:
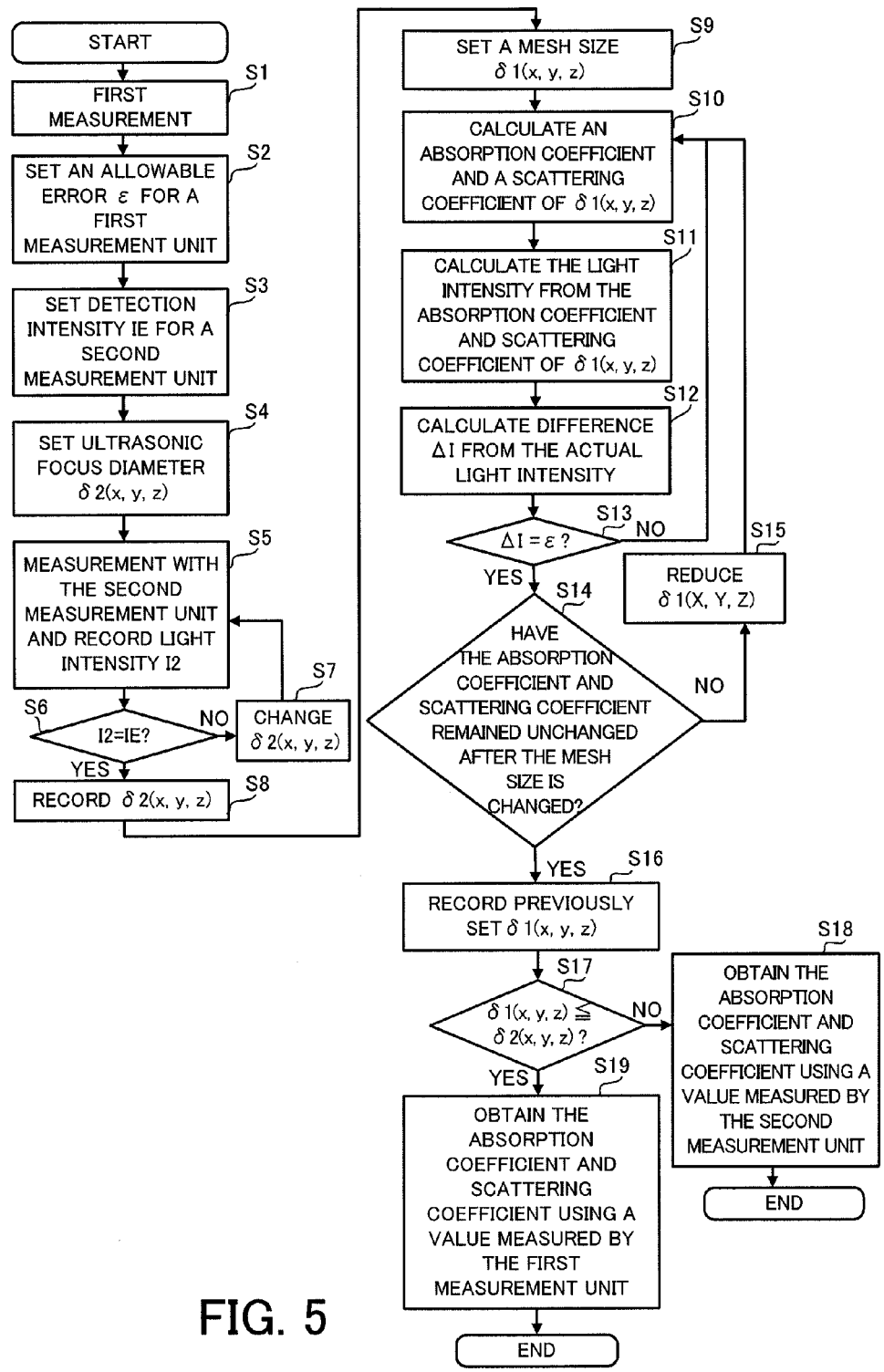
FIG. 5 is a flowchart of a measurement method performed by a controller shown in FIG. 1A.

Referring now to FIG. 5, a description will be given of a measurement method executed by the controller 1. FIG. 5 is a flowchart for explaining the measurement method executed by the controller 1. In FIG. 5, "S" denotes the step. In an example, FIG. 5 executes the first or DOT measurement, the second or AOT measurement, the image reconstruction, and a comparison of the measurement size. The signal processor 6 rather than the controller 1 may perform one or more of the following steps.

Initially, the controller 1 performs the first or DOT measurement (S1). The first measurement does not set a mesh size unlike the following image reconstruction, irradiates the light from the light source 3 via the fiber 11 into the measurement container 15, and detects the light using the photodetectors 13. In this embodiment, the "mesh" is a (minimum) division unit of the test region. For operational purposes, the test region is divided into the mesh size and at least one of the scattering characteristic and the absorption characteristic is calculated for each of the divided areas.

Next, the controller 1 sets an allowable error $\epsilon$ in the first measurement unit (S2). This is a permissible value of a difference between the signal intensity detected by the photodetector 13 and the signal intensity calculated in the reconstruction in the test object 10. In other words, until the value reaches the allowable error $\epsilon$, the mesh size $\delta 1$ or the measurement size can be reduced in the following DOT measurement. S2 may be performed just before S9 or just after S1. The allowable error $\epsilon$ may be previously set and stored in the memory 5. In this embodiment, the allowable error $\epsilon$ is empirically set by an operator of the measurement apparatus and the controller 1 recognizes the set allowable error $\epsilon$, but the controller 1 may automatically set it through an operation using a variety of conditions input in the memory 5.

S3-S8 are the steps of the second or AOT measurement for a specific location (x, y, z). Initially, the controller 1 sets the light intensity IE that provides an advantageous SN ratio from the minimum intensity limit measurable by the photodetector in the second measurement (S3). S3 may be performed in advance and the IE may be stored in the memory 5. The light intensity IE is high enough to detect a test region, such as a cancer, and higher than the noise level Iw of the photodetector 13.

Next, the controller 1 sets a focus diameter $\delta 2(x, y, z)$ of the ultrasonic focus region 17 (S4). An initial value of the focus diameter $\delta 2(x, y, z)$ may be set automatically by the controller 1 or by default, or an operator of the measurement apparatus may set it and the controller 1 may recognize the set $\delta 2(x, y, z)$. The controller 1 performs the second measurement with the set $\delta 2(x, y, z)$, and records the light intensity I2 detected by the photodetectors 13, in the memory 5 (S5).

Next, the controller 1 compares the light intensity IE determined by the detection limit of the photodetector 13 with the obtained light intensity I2 (S6), and stores $\delta 2(x, y, z)$ set in S4 in the memory 5 (S8) when the controller 1 determines that both have the same value (Yes of S6). According to this embodiment, the controller 1 obtains the focus diameter $\delta 2(x, y, z)$ of the ultrasonic focus region 17 from the ultrasonic transducer array 12. The controller 1 may previously set an allowable error $\epsilon 1$ and consider that I2 is equal to IE when a difference between I2 and IE falls within the allowable error range. In this case, |I2-IE| as a difference between I2 and IE may be equal to or smaller than $\epsilon 1$ but $0 \leq I2-IE \leq \epsilon 1$ may be set because it is undesirable that I2 is smaller than IE. When the controller 1 determines that they are different values (No of S6), the controller 1 changes the focus diameter $\delta 2(x, y, z)$ of the ultrasonic focus region 17 (S7) and repeats this flow until their values become equal to each other. The second measurement by the second measurement unit thus ends.

S9-S16 are the image reconstruction steps. Initially, the controller 1 sets a mesh size $\delta 1(x, y, z)$ of a specific location (x, y, z) (S9). An initial value of the focus diameter $\delta 1(x, y, z)$ may be set automatically by the controller 1 or by default, or an operator of the measurement apparatus may set it and the controller 1 may recognize the set $\delta 1(x, y, z)$. In this embodiment, each mesh has a square shape, as shown in FIGS. 7A-7C, and each side of the square is $\delta 1(x, y, z)$. However, the present invention is not limited in having a square as the shape of each mesh but may use a different polygon, such as a hexagon. The polygon may be a regular polygon, in which each side has the same length. There may be provided means for enabling the operator of the measurement apparatus to set the mesh shape.

When the set mesh size $\delta 1(x, y, z)$ is large, a solution does not converge. The mesh size $\delta 1(x, y, z)$ is a (minimum) division unit used for the first measurement unit to reconstruct an image of the inside of the test object 10, and each mesh is provided with one absorption coefficient and one scattering coefficient. The mesh size can be made smaller to increase the number of solutions conveniently so that the solution can accord with the measurement value. However, even when the mesh size is reduced, the absorption coefficient and the scattering coefficient may sometimes remain unchanged. This is the resolution (measurement size) of the first measurement unit.

The image reconstruction of this embodiment utilizes the light diffusion equation and the finite element method to estimate the absorption coefficient and the scattering coefficient. The medium in the measurement container 15 or the test object 10 is divided into meshes each having a size $\delta 1(x, y, z)$, and a coordinate (i, j) of each mesh is provided with an absorption coefficient $\mu_a^{ij}$ and a scattering coefficient $\mu_s^{ij}$. For a distribution $P_{ij}(\mu_a^{ij}, \mu_s^{ij})$ of the absorption coefficient and the scattering coefficient of the test object 10, the light intensity I1 is calculated by turning the first measurement into a model with a function $f$ based on the light diffusion equation, as in the following equation:

$$f(r,\omega,S_0) \cdot P_{ij}(\mu_a^{ij},\mu_s^{ij}) = I1 \qquad \text{Equation 6}$$

The distribution $P_{ij}(\mu_a^{ij}, \mu_s^{ij})$ of the absorption coefficient and the scattering coefficient is set and optimized until a difference between the light intensity I1 calculated based on Equation 6 at each position of each photodetector 13 and the actual measurement value falls within the allowable error $\epsilon$.

Next, the controller 1 sets one absorption coefficient and one scattering coefficient to a specific δ1(x, y, z) (S10). For example, assume that δ1(x, y, z) shown in FIG. 7A is used at this time. In the meanwhile, in FIGS. 7A-7C, meshes having different designs have different absorption coefficients and scattering coefficients. The reconstruction is provided with the first mesh size shown in FIG. 7A and one absorption coefficient and one scattering coefficient. FIG. 7A shows that a predetermined test region is divided into four square meshes each having the same size.

The controller 1 calculates the light intensity I1 calculated from the absorption coefficient and the scattering coefficient (S11), and calculates a difference ΔI (=|I1−Im|) between the calculated light intensity I1 and the actually measured light intensity Im (S12). When the controller 1 determines that the difference ΔI is larger than the allowable error ε (No of S13), the flow returns to S10. The controller 1 may inform the operator of the measurement apparatus of the abnormality when the loop of the steps S10-S13 has been repeated threshold times or more.

On the other hand, when the controller 1 determines that the difference ΔI is smaller than the allowable error ε (Yes of S13), the controller 1 compares the absorption coefficient and scattering coefficient with those of the previously set mesh size (S14). When the controller 1 determines that the absorption coefficient and the scattering coefficient of the currently set mesh size change from those of the previously set mesh size (No of S14), the controller 1 reduces the current mesh size (S15). In S14 of this embodiment, the controller 1 determines that there is a change when the differences exceed the thresholds. In this case, the controller 1 may address the absorption coefficient and the scattering coefficient of only one mesh or the controller 1 may weigh a plurality of meshes or all meshes. The controller 1 may determine that there is a change when the absorption coefficient and the scattering coefficient of one addressed mesh change even when other meshes do not change, or when a majority of meshes change. Moreover, when δ1(x, y, z) is initially set, the previous comparison test object does not exist and the flow is configured to always transfer from S14 to S15. For example, the controller 1 reduces the mesh size as shown in FIG. 7B, and compares the absorption coefficient and the scattering coefficient of the mesh size shown in FIG. 7B with those of the mesh size shown in FIG. 7A (S14). Even in FIG. 7B, each mesh has the same size.

When the controller 1 determines that the absorption coefficient and the scattering coefficient of the mesh size shown in FIG. 7B change from those of the mesh size shown in FIG. 7A (No of S14), the controller 1 further reduces the mesh size as shown in FIG. 7C (S15). The controller 1 then compares the absorption coefficient and the scattering coefficient of the mesh size shown in FIG. 7C with those of the mesh size shown in FIG. 7B (S14). Even in FIG. 7C, each mesh has the same size. When the controller 1 determines that the absorption coefficient and the scattering coefficient of the currently set mesh size do not change from those of the previously set mesh size (Yes of S14), the controller 1 stores the previously set mesh size δ1(x, y, z) in the memory 5 (S16). In this embodiment, the controller 1 determines that the absorption coefficient and the scattering coefficient of the mesh size shown in FIG. 7C do not change from those shown in FIG. 7B (Yes of S14). Therefore, the controller stores the mesh size δ1(x, y, z) shown in FIG. 7B in the memory 5 (S16). As a result, the mesh size δ1 shown in FIG. 7B becomes the resolution (measurement size) of the first measurement unit. In this embodiment, the controller 1 obtains the mesh size δ1(x, y, z) as a (minimum) division unit of the test region from the detection results of the photodetectors 13.

Figure 8:
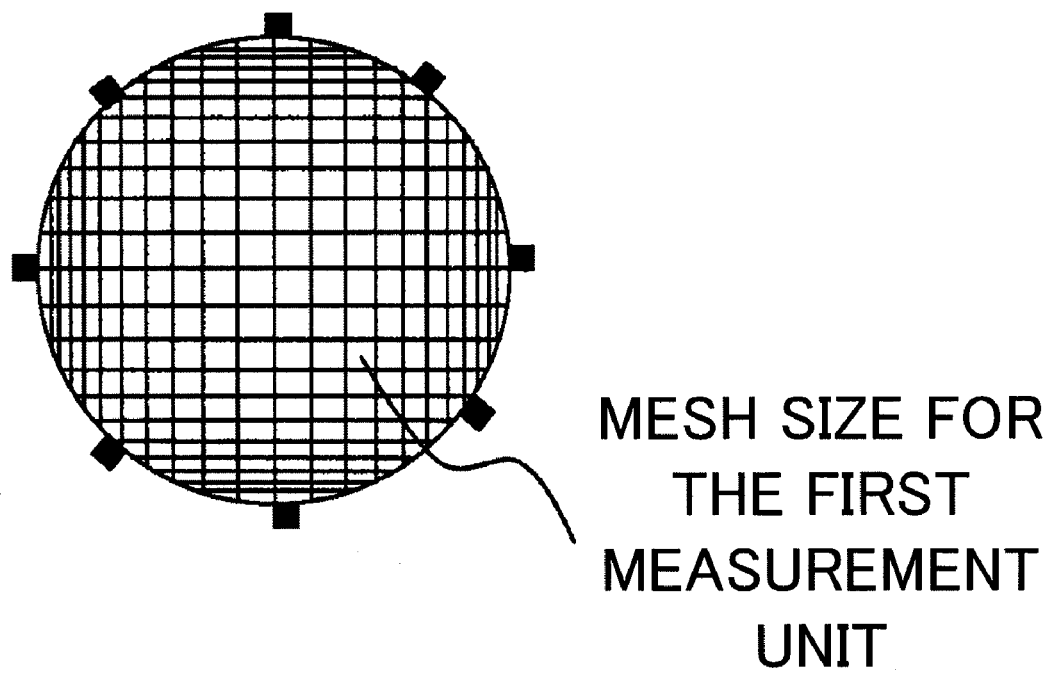
FIG. 8 shows a mesh size $\delta 1(x, y, z)$ of the first measurement unit in the first embodiment.

FIG. 8 shows the mesh size δ1(x, y, z) measured by the first measurement unit. In general, the mesh size needs to be increased as the test region becomes more distant from the surface of the test object 10 so as to increase the light intensity.

Next, the controller 1 compares the focus diameter δ2(x, y, z) recorded in S8 with the mesh size δ1(x, y, z) recorded in S16 (S17). As described above with reference to FIGS. 6 to 7C, the focus diameter δ2(x, y, z) is a diameter of a circle and the mesh size δ1(x, y, z) is a length of one side of a square. The controller 1 of this embodiment may compare their areas (i.e., πδ2²(x, y, z)/4 and δ1²(x, y, z)) with each other in S17.

When the controller 1 determines that the focus diameter δ2(x, y, z) is smaller (No of S17), the controller 1 calculates the absorption coefficient and the scattering coefficient by using the value measured by the second measurement unit (S18). The absorption coefficient and the scattering coefficient can be calculated by using a modulation depth M and the change rate of each of the ultrasonic amplitude A and the frequency $f_a$, i.e., $\partial M/\partial A$ and $\partial M/\partial f_a$.

An autocorrelation function of the light modulated by the ultrasonic wave can be expressed as follows using a probability density function p(s) of an optical path length s [mm] and the scattering field Es:

$$G_1(\tau) = \int_0^\infty p(s)\langle E_S(t)E_S^*(t+\tau)\rangle ds \quad \text{Equation 7}$$

The probability density function p(s) in Equation 7 is a function that also depends upon the absorption coefficient $\mu_a$ [mm$^{-1}$], the scattering coefficient $\mu_s$ [mm$^{-1}$], and the anisotropic parameter g in addition to the optical path length s.

When coherent light propagates in a homogeneous medium irradiated with a plane ultrasonic wave, the autocorrelation function at time τ [sec] in the electric field of the scattered light can be written as follows:

$$G_1(\tau) = C\frac{\sinh(z_0\sqrt{(S_U+S_B+\mu_a)D^{-1}})}{\sinh(L_0\sqrt{(S_U+S_B+\mu_a)D^{-1}})} \quad \text{Equation 8}$$

$$C = \frac{\sinh(L_0\sqrt{\mu_a D^{-1}})}{\sinh(z_0\sqrt{\mu_a D^{-1}})} \quad \text{Equation 9}$$

$$S_U = \frac{1}{2}(2n_0 k_0 A)^2 \sin^2(\omega_a \tau/2)(\delta_n + \delta_d) \quad \text{Equation 10}$$

$$S_B = 2\tau/(\tau_0 l^*) \quad \text{Equation 11}$$

Equation 10 indicates the influence of the ultrasonic interaction, and Equation 11 indicates the influence of Brownian motion. Here, D is a diffusion coefficient (=⅓$\mu_s'$) [mm], $n_0$ is the refractive index of a medium, $k_0$ is the wave number of the light in vacuum [mm$^{-1}$], $\omega_a$ is the ultrasonic angular frequency (=2π$f_a$), and l is a mean free path (=1/$\mu_s$) [mm]. l*=l/(1−g) [mm]. L is the thickness of the medium [mm]. $L_0$=L+2l*γ is a distance between extrapolation boundaries [mm]. $Z_0$=l*(1+γ) [mm]. γ=0.7104. $\tau_0$ is the relaxation time of one particle in Brownian motion [sec]. $\delta_n$ and $\delta_d$ are refractive index changes and the displacement of the scatter material due to the change of the ultrasonic phase.

The autocorrelation function expressed by Equation 8 is Fourier-transformed into the following Equation 12 to calculate the modulation depth M:

$$I_n = \frac{1}{T_a} \int_0^{T_a} \cos(n\omega_a \tau) G_1(\tau) d\tau \qquad \text{Equation 12}$$

$$M = \frac{I_1}{I_0} \qquad \text{Equation 13}$$

Here, Ta is the ultrasonic period [sec].

The thus calculated modulation depth corresponds to a ratio between an AC signal and a DC signal obtained by the measurement apparatus.

The ultrasonic frequency used for the biological measurements and medial examinations is about MHz, and each hyperbolic sine function in the Equations 8 and 9 can be linearly developed and approximated in the ultrasonic amplitude (energy) below the ultrasonic irradiation safety standard of a diagnosis. In addition, when $\tau = T_a/2$ is substituted and arranged in the measurement system in which an effect of the Brownian motion is negligible.

$$1 - G_1(T_a/2) = \frac{L_0^2}{6D}\left\{\frac{1}{2}(2n_0k_0A)^2(\delta_n + \delta_d) + \mu_a\right\} \qquad \text{Equation 14}$$

When Equation 14 is differentiated with respect to A and $f_a$ and arranged so as to solve for the equivalent scattering coefficient μs' and the absorption coefficient μa, the following equation is obtained:

$$\mu_s' = \frac{1}{n_0 k_0 A L_0} \sqrt{\frac{\frac{\partial}{\partial A}[1 - G_1(T_a/2)]A - \frac{\partial}{\partial f_a}[1 - G_1(T_a/2)]f_a}{\frac{1}{3} + \frac{2}{5}\frac{(2\pi n_0 k_0 A L_0 \eta / v_a)^2 f_a}{\frac{\partial}{\partial f_a}[1 - G_1(T_a/2)]}}} \qquad \text{Equation 15}$$

$$\mu_a = \frac{2}{L_0^2 \mu_s'}\left([1 - G_1(T_a/2)] - \frac{\partial}{\partial A}[1 - G_1(T_a/2)]\frac{A}{2}\right) \qquad \text{Equation 16}$$

Here, $\eta(=(\partial n/\partial p)\rho v_a^2)$ is the photoelastic coefficient, and $v_a$ is the sound velocity [mm/sec].

It is understood that the scattering coefficient and the absorption coefficient can be obtained from the modulation depth M and a change rate ∂M/∂A of the modulation depth M to the ultrasonic amplitude or the change rate ∂M/∂fa of the modulation depth M to the ultrasonic frequency.

On the other hand, when the controller determines that the mesh size δ1(x, y, z) is smaller (Yes of S17), the controller 1 calculates the absorption coefficient and the scattering coefficient using the value measured by the first measurement unit (S19). The controller 1 repeats this flow for each measurement position.

Thus, in this embodiment, the controller 1 selects one of the first measurement unit and the second measurement unit based on a result of comparing the mesh size or its corresponding value with the focus diameter of the ultrasonic focus value 17 or its corresponding value.

When AOT and DOT are combined and complimentarily used in accordance with the above flow, the estimation accuracy of the distributions of the absorption coefficient and the scattering coefficient and the spatial resolution can be improved. A physical model used to calculate the light propagation in the image reconstruction may use a model in accordance with the diffusion equation, or a light propagation model utilizing the Monte Carlo simulation, or the transport equation of the photon.

The spectroscopic information can be obtained by preparing as the light source 3 a light source configured to provide a plurality of wavelengths and by executing the similar measurement and process for each wavelength. Ratios of major ingredients of the test object 10, such as oxygenated hemoglobin, reduced hemoglobin, water, fat, and collagen, can be calculated by utilizing the Lambert-Beer law and the data of the absorption coefficient for each wavelength, and other functional information, such as an oxygen saturation index, can also be calculated from the hemoglobin concentration. The functional information is mapped with a coordinate of the ultrasonic focus region 17, and visualized and displayed as image data on the display 7.

While this embodiment commonly utilizes the photodetectors 13 for the first measurement unit and the second measurement unit, the first measurement unit and the second measurement unit may use different photodetectors, although the standardization of the photodetector can reduce an error which would otherwise occur due to the device differences.

Second Embodiment

As described above, the measurement size of the first measurement can be estimated to about 10% of the optical path length once the test object 10 is determined, and thus the second embodiment simplifies the flow of FIG. 5 by eliminating the loop used to determine the mesh size δ1(x, y, z). The estimation can be made by utilizing the size of the test object 10, and the average absorption coefficient and scattering coefficient in the test object 10. The mean absorption coefficient and scattering coefficient can be calculated, for example, from the diffusion equation or Monte Carlo simulation utilizing the light intensity detected in the first measurement unit. The measurement apparatus of this embodiment can use the measurement apparatus 100 shown in FIG. 1 as it is.

Figure 9:
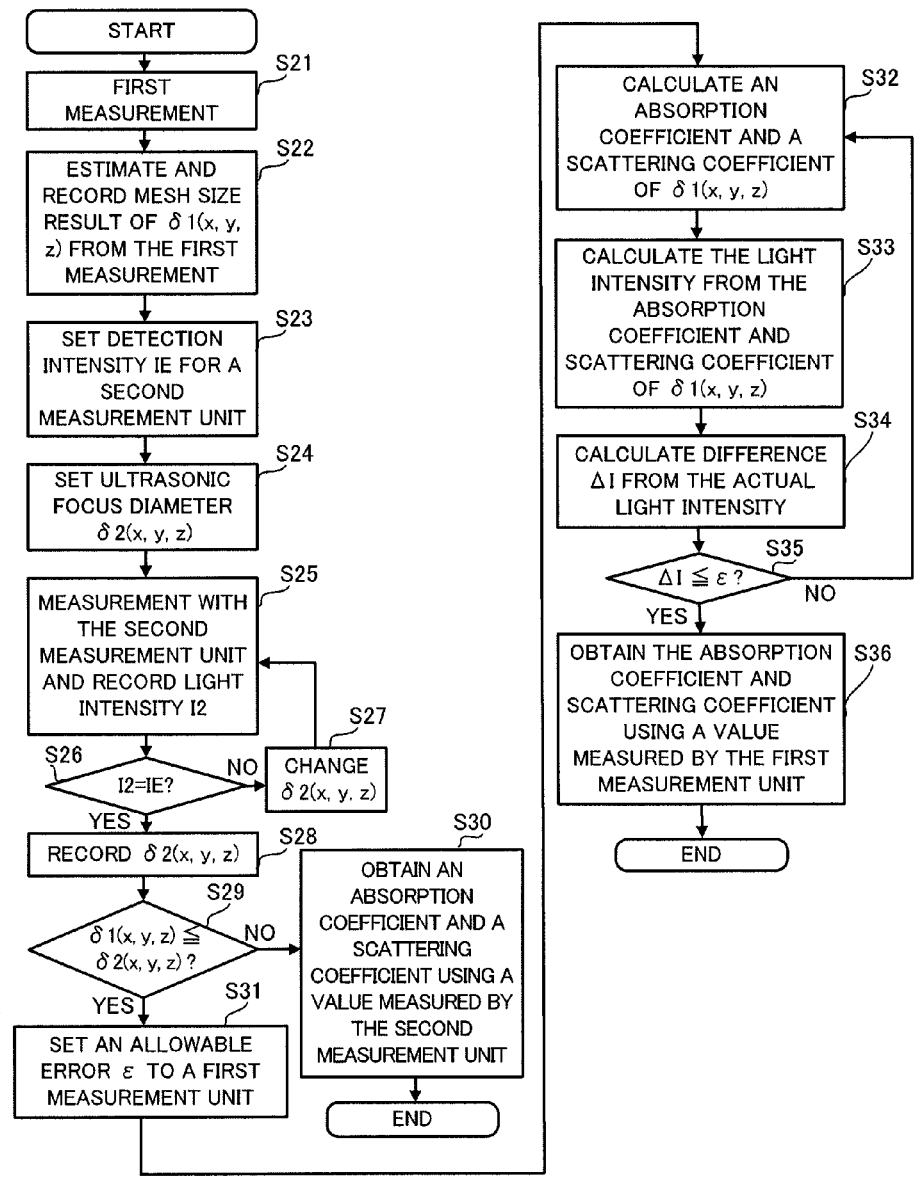
FIG. 9 is another flowchart of a measurement method performed by the controller shown in FIG. 1A.

FIG. 9 is a flowchart for explaining the measurement method executed by the controller 1 according to this embodiment. In FIG. 9, "S" denotes "step". The signal processor 6 rather than the controller 1 may perform one or more of the following steps.

Initially, the controller 1 performs the first or DOT measurement (S21). S21 is similar to S1. The first measurement does not set a mesh size unlike the following image reconstruction, irradiates the light from the light source 3 through the fiber 11 into the measurement container 15, and detects the light using the photodetectors 13.

Next, the controller 1 estimates, based on the optical path length of the light in the test object, the mesh size δ1(x, y, z) that is a (minimum) division unit of the test region (S22).

S23-S28 are the steps for the second or AOT measurement to a specific location (x, y, z), and correspond to the steps S3-S8. Initially, the controller 1 sets the light intensity IE that provides an advantageous SN ratio, from the minimum intensity limit measurable by the photodetector in the second measurement (S23). Next, the controller 1 sets a focus diameter δ2(x, y, z) of the ultrasonic focus region 17 (S24). The controller 1 performs the second measurement with the set δ2(x, y, z), and records the light intensity I2 detected by the photodetector 13, in the memory 5 (S25).

Next, the controller 1 compares the light intensity IE determined by the detection limit of the photodetector 13 with the obtained light intensity I2 (S26), and stores δ2(x, y, z) set in S24 in the memory 5 (S28) when the controller 1 determines that both have the same value (Yes of S26). According to this embodiment, the controller 1 obtains the focus diameter δ2(x, y, z) of the ultrasonic focus region 17 from the ultrasonic transducer array 12. When the controller 1 determines that they are different values (No of S26), the controller 1 changes the focus diameter δ2(x, y, z) of the ultrasonic focus region 17 (S27), and repeats this flow until their values become equal to each other. The second measurement by the second measurement unit thus ends.

Next, the controller 1 compares the focus diameter δ2(x, y, z) recorded in S28 with the mesh size δ1(x, y, z) recorded in S22 (S29). S29 corresponds to S17. When the controller 1 determines that the focus diameter δ2(x, y, z) is smaller (No of S29), the controller 1 calculates the absorption coefficient and the scattering coefficient by using the value measured by the second measurement unit (S30). On the other hand, when the controller determines that the mesh size δ1(x, y, z) is smaller (Yes of S29), the controller 1 calculates the absorption coefficient and the scattering coefficient using the value measured by the first measurement unit. Thus, in this embodiment, the controller 1 selects one of the first measurement unit and the second measurement unit based on a result of comparing the mesh size or its corresponding value with the focus diameter of the ultrasonic focus value 17 or its corresponding value.

Initially, the controller 1 sets an allowable error ε to the first measurement unit (S31). S31 corresponds to S2. Next, the controller 1 executes S32 to S35 similar to S10 to S13, but does not perform S14-S16 because it has already estimated the mesh size δ1(x, y, z) in S22. When the controller 1 determines that the difference ΔI is smaller than the allowable error ε (Yes of S35), the controller 1 calculates the absorption coefficient and the scattering coefficient using the value measured by the first measurement unit (S36). S36 corresponds to S19.

Figure 10:
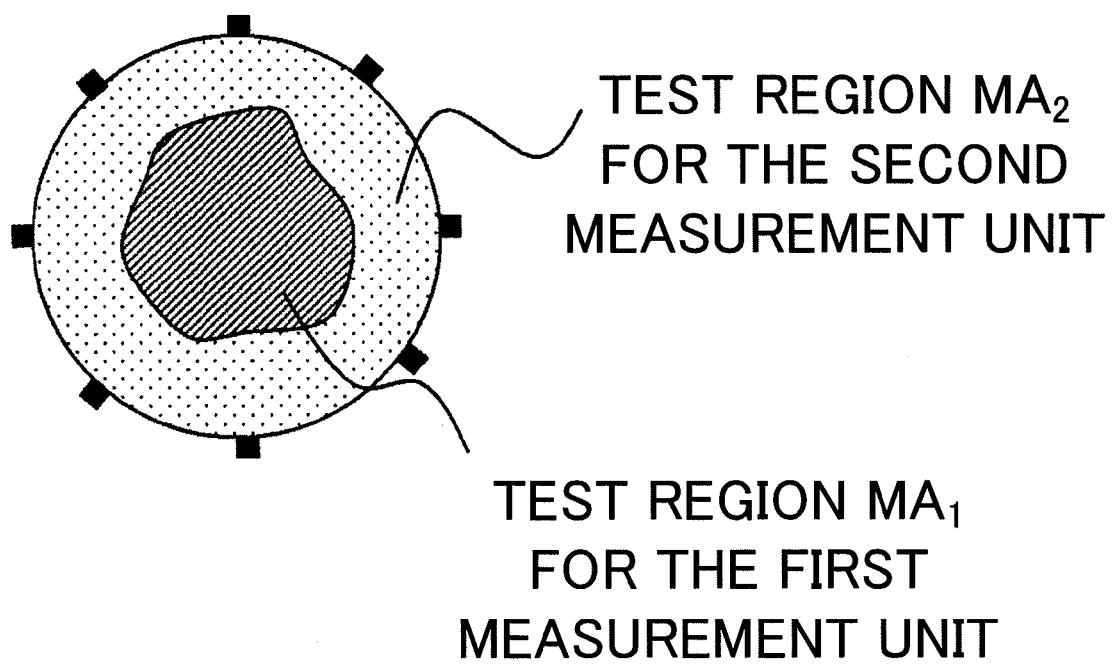
FIG. 10 is a sectional view of the test object showing the first measurement region and the second measurement region in the second embodiment.

The above flow is repeated for each measurement position, but once the controller 1 determines that δ1(x, y, z) is smaller than δ2(x, y, z) in S29, the controller 1 uses the first measurement unit to calculate the absorption coefficient and the scattering coefficient for the test region inside of that position in the test object 10. The second measurement is no longer performed, the region MA1 for the first measurement is separated from the region MA2 for the second measurement, and the resolution improves and the measurement time shortens. For simplicity, FIG. 10 shows that the test object 10 spreads over the measurement container 15 with no matching member 9, similar to FIG. 3.

The division is not limited to an exclusive use of a comparison of the resolution (measurement size). For example, the absorption coefficient and the scattering coefficient in the test object 10 are calculated by the first measurement, and the second measurement may be used if there is an additional test region to be carefully inspected, such as a tumor or an apparently abnormal lesion. Thereby, the measurement time can be shorter than the careful inspection of the entire body with a high resolution. In addition, more precise absorption coefficient and scattering coefficient may be supplemented from the two types of the absorption coefficient and the scattering coefficient obtained by the first measurement and the second measurement.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims foreign priority benefit based on Japanese Patent Application 2008-241210, filed on Sep. 19, 2008, which is hereby incorporated by reference herein in its entirety as if fully set forth herein.

What is claimed is:

1. A measurement apparatus comprising:
a first measurement unit configured to measure a spectroscopic characteristic in a test region in an object, by applying diffused optical tomography;
a second measurement unit configured to measure a spectroscopic characteristic in an ultrasonic focus region in the object by applying acousto-optical tomography; and
a controller configured to calculate at least one of an absorption characteristic and a scattering characteristic in the object by utilizing one of said first measurement unit and said second measurement unit, which has a measurement size corresponding to a smaller one of a size of a mesh that is a division unit of the test region and a focus diameter of the ultrasonic focus region, said first measurement unit having a measurement size corresponding to the size of the mesh, and said second measurement unit having a measurement size corresponding to the focus diameter,
wherein said first measurement unit includes a first photodetector configured to detect light that has passed inside of the object and then emitted from the object, and
wherein said second measurement unit includes an ultrasonic transducer configured to focus and irradiate an ultrasonic wave upon the ultrasonic focus region.

2. The measurement apparatus according to claim 1, wherein said controller estimates the size of the mesh from an optical path length of the light in the object.

3. The measurement apparatus according to claim 1, wherein said controller uses said second measurement unit for the test region that contains a border between a measurement by said first measurement unit and a measurement by said second measurement unit, and said controller reconstructs an image of the border using a measurement result by said first measurement unit.

4. The measurement apparatus according to claim 1, wherein said controller obtains the size of the mesh.

5. The measurement apparatus according to claim 1, wherein said controller obtains the focus diameter of the ultrasonic focus region.

6. The measurement apparatus according to claim 1, wherein said controller obtains the size of the mesh and the focus diameter of the ultrasonic focus region.

7. The measurement apparatus according to claim 1, wherein said second measurement unit includes a second photodetector configured to detect modulated light among light that has passed inside of an object and emitted from the object.

8. A measurement method comprising:
calculating at least one of an absorption characteristic and a scattering characteristic in a test region in an object that is an absorption scattering medium, using a first measurement unit that is configured to measure a spectroscopic characteristic in the object utilizing diffused optical tomography and that includes a photodetector configured to detect light that has passed inside of the object and is emitted outside of the object;
calculating at least one of the absorption characteristic and the scattering characteristic in an ultrasonic focus region in the object using a second measurement unit that is configured to measure the spectroscopic characteristic in the object utilizing acousto-optical tomography, and that includes an ultrasonic transducer configured to focus and irradiate an ultrasonic wave upon the focus region; and selecting one of the first measurement unit and the second measurement unit which one has a smaller measurement size from a size of the mesh that is a division unit of the test region and the focus diameter of an ultrasonic focus region from the ultrasonic transducer.

9. The measurement method according to claim 8, further comprising obtaining the size of a mesh.

10. The measurement method according to claim 8, further comprising obtaining the focus diameter.

11. The measurement method according to claim 8, further comprising obtaining the size of a mesh and the focus diameter.

12. A measurement method comprising steps of: selecting one of a first measurement unit configured to measure a spectroscopic characteristic in a test region in an object utilizing diffused optical tomography and that includes a photodetector configured to detect light that has passed inside of the object and is emitted outside of the object, and a second measurement unit configured to measure the spectroscopic characteristic in an ultrasonic focus region in the object utilizing acousto-optical tomography and that includes an ultrasonic transducer configured to focus and irradiate an ultrasonic wave upon the ultrasonic focus region, the selected one of the first measurement unit and the second measurement unit having a smaller measurement size than a size of a mesh that is a division unit of the test region and a focus diameter of the ultrasonic focus region from the ultrasonic transducer; and obtaining at least one of an absorption characteristic and a scattering characteristic in the object utilizing the selected one of the first measurement unit and the second measurement unit having the smaller measurement size.

* * * * *